US005849324A

United States Patent [19]

Dohnalek et al.

[11] Patent Number: 5,849,324

[45] Date of Patent: *Dec. 15, 1998

[54] USE OF INDIGESTIBLE OLIGOSACCHARIDES TO REDUCE THE INCIDENCE OF OTITIS MEDIA IN HUMANS

[75] Inventors: Margaret Ione Halpin Dohnalek, Worthington; Karin Margaret Ostrom, Reynoldsburg; Milo Duane Hilty, Lewis Center, all of Ohio

[73] Assignee: Abbott Laboratories, Abbott Park, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 653,083

[22] Filed: Jun. 12, 1996

Related U.S. Application Data

[60] Provisional application No. 60/001,000 Jul. 10, 1995.

[51] Int. Cl.[6] .................................................. A61K 9/68
[52] U.S. Cl. .................... 424/440; 424/442; 424/197.11; 424/195.1; 424/441; 514/54; 426/73; 426/333.3
[58] Field of Search ............................ 424/197.11, 195.1, 424/440, 441, 42; 426/73, 333.3; 514/54

[56] References Cited

U.S. PATENT DOCUMENTS

| 4,681,771 | 7/1987 | Adachi et al. ........................... 426/658 |
|---|---|---|
| 4,859,488 | 8/1989 | Kan ......................................... 426/658 |
| 5,021,245 | 6/1991 | Borschel et al. ........................... 426/2 |
| 5,206,355 | 4/1993 | Richards et al. ......................... 536/4.1 |
| 5,219,842 | 6/1993 | Okada et al. .............................. 514/54 |
| 5,318,794 | 6/1994 | Richards .................................. 426/658 |
| 5,437,880 | 8/1995 | Takaichi et al. ........................... 426/73 |

FOREIGN PATENT DOCUMENTS

94/27618  12/1994  WIPO.

OTHER PUBLICATIONS

Hidaka, et al., "Effects of Fructooligosaccharides on Intestinal Flora and Human Health," *Bifidobacteria Microflora* 5(1):37–50, 1986.

Hidaka, et al., "The Effects of Undigestible Fructooligosaccharides on Intestinal Microflora and Various Physiological functions on Human Health," *New Developments in Dietary Fiber*, 105–177, 1990.

Hata and Nakajima, "Studies on Relationship Between Intake of Fructooligosaccharides and Abdominal Symptoms–Estimation of the Maximum Non–Effective Dose and 50% Laxative Effective Dose," *Geriatric Medicine,* vol. 23, No. 5: 817–828, 1985.

Tanaka, et al., "Utilization of Fructo–oligosaccharide from Mai–Meng–Dong by Intestinal Flora", Shoyakugaku Zasshi, 42(2), 143–146, 1988.

Coppa, et al., "Preliminary Study of Breastfeeding and Bacterial Adhesion to Uroepithelial Cells," abstr. *The Lancet,* vol. 335, 569–571, 1990.

Hidaka et al., "Proliferation of Bifidobacteria by Oligosaccharides and Their Useful Effect on Human Health," *Bifidobacteria Microflora,* vol. 10 (1), 65–79, 1991.

Hidaka, et al., "Fructooligosaccharides: Enzymatic preparation and Biofunctions," *Journal of Carbohydrate Chemistry,* 10(4): 509–522, 1991.

Speights, et al., "Fructooligosaccharides—A Low Caloric Building Agent—And More From Sucrose," *Carbohydrates in Industrial Synthesis,* ed. M.A. Clarke, Proceedings of the Symposium of the Division of Carbohydrate Chemistry of the American Chemical Society, 1992.

Kunz and Rudloff, "Biological functions of oligosaccharides in human milk," *Acta Paediatr,* 82:903–12 (1993).

Clevenger, et al., "Toxicological evaluation of neosugar: genotoxicity, carcinogenicity, and chronic toxicity," *Journal of the American College of Toxicology,* 7:643–662, 1988.

Primary Examiner—Thurman K. Page
Assistant Examiner—D. Faulkner
Attorney, Agent, or Firm—Thomas D. Brainard; J. Michael Dixon

[57] ABSTRACT

A method is provided for reducing the incidence of otitis media in infants and young children by enterally administering indigestible fructooligosaccharides. More specifically, the present invention relates to a method for reducing the incidence of otitis media comprising administering to humans an indigestible fructooligosaccharide selected from the group consisting of 1-kestose, nystose and 1-$^F$-B-fructofuranosyl nystose. The indigestible fructooligosaccharides can be produced through enzymatic synthesis, chemical techniques or isolated from plant materials and are administered in the form of a nutritional product, candy, tablets, chewing gums, lozenges, milk products, yogurts and the like. In a preferred embodiment of this invention, the fructooligosaccharides have a DP of 2 to 20 and still more preferably are the fructooligosaccharides $FG_2$, $GF_3$, and $GF_4$.

13 Claims, No Drawings

USE OF INDIGESTIBLE OLIGOSACCHARIDES TO REDUCE THE INCIDENCE OF OTITIS MEDIA IN HUMANS

This application claims benefit of U.S. Provisional Application No. 60/001,000 filed Jul. 10, 1995.

FIELD OF THE INVENTION

The present invention relates to a method for reducing the incidence of otitis media by enterally administering to humans an indigestible oligosaccharide.

BACKGROUND OF THE INVENTION

Prevention of otitis media in young children is a significant public health problem that has not been solved. Methods of prevention presently available are limited to practices that reduce transmission of infectious agents to susceptible individuals. Such methods include provision of clean water, hand washing, and good personal hygiene. The development of effective vaccines to prevent otitis media has been limited because of the large number of potential pathogens that can cause this disease and because young children, who are at greatest risk, often fail to develop effective immunity. Individuals treated with antibiotics for otitis media and other infectious diseases may become colonized with antibiotic-resistant bacteria and may not respond to antibiotic treatment.

Fructooligosaccharides (FOS) are natural substances composed primarily of fructose molecules. They belong to a group of carbohydrates that occur in many different plants. FOS are indigestible oligosaccharides that pass through the small intestine without being digested, reaching the large intestine where they are selectively fermented by certain microorganisms. FOS can be utilized efficiently by lactobacilli and bifidobacteria, species of bacteria that are beneficial for human health (Hidaka et al.). Selective fermentation of FOS by bifidobacteria leads to an increase in the presence of these bacteria and to the production of acetic acid and lactic acid as fermentation endproducts, resulting in a lower pH in the digestive tract and providing a means to prevent the overgrowth of harmful bacteria like *Escherichia coli, Clostridium perfringens* and *Clostridium difficile*. (Hidaka et al., "Fructooligosaccharides: Enzymatic Preparation and Biofunctions", *Journal of Carbohydrate Chemistry* 10(4): 509–522, 1991).

Indigestible Oligosaccharides

"Indigestible oligosaccharides" refers to a small carbohydrate moiety that is resistant to endogenous digestion in the human upper digestive tract. Fructooligosaccharides (FOS) are indigestible oligosaccharides that are members of the inulin subclass of fructosans, polymers composed of fructose residues. FOS are sometimes characterized by their degree of polymerization. Degree of Polymerization (DP) means the number of covalent bonds between the monosaccharide units in the polymer. For example, the tetramer nystose is composed of three fructose monomers bound to glucose (or sucrose plus two fructose units) and has a DP of 3. Using this nomenclature, sucrose is $GF_1$(glucose plus fructose). Specifically, inulins are glucofructosans, carbohydrate polymers consisting of a chain of fructose residues linked by $(2\rightarrow1)$-$\beta$-glycosidic bonds and usually having a single D-glycosyl residue linked $(1\rightarrow2)$-$\alpha$- to the first fructose molecule.

Fructooligosaccharides (FOS) can be produced enzymatically, through chemical techniques or by extraction from natural substances. FOS occur in nature in many kinds of plants, including onions, garlic, shallots, artichokes, wheat, rye, bananas, asparagus and tomatoes, that are commonly part of a human diet (Speights et al., "Fructooligosaccharides-A Low Caloric Bulking Agent-And More From Sucrose", *Carbohydrates in Industrial Synthesis,* ed. M. A. Clarke, Proceedings of the Symposium of the Division of Carbohydrate Chemistry of the American Chemical Society, 1992). Another natural source of FOS is the chicory root. FOS can also be synthesized from sucrose through the use of transfructosylating enzymes. Treatment of 50% (w/v) sucrose with the transfructosylating enzyme from *Aspergillus niger* results in a mixture of fructooligosaccharides containing 2,3, or 4 fructose residues, designated respectively: 1-kestose or $GF_2$ in which one molecule of fructose is bound to sucrose; nytrose or $GF_3$ in which two molecules of fructose are bound to sucrose; and $1^F$-$\beta$-fructofuranosyl nystose or $GF_4$ in which three molecules of fructose are bound to sucrose.

An enzymatic method of producing FOS industrially is disclosed in U.S. Pat. No. 4,681,771 to Adachi et al. that comprises reacting sucrose in the presence of a fructosyltransferase (enzyme) to obtain $GF_2$, $GF_3$, $GF_4$, and $GF_5$. The source for the enzyme, fructosyltransferase, could be a fungus such as *Aspergillus niger.*

Richards (U.S. Pat. No. 5,318,794) discloses a method for producing a product (caramel) containing between 20 and 50% fructose oligosaccharides, having a degree of polymerization (DP) of about 3–10. The method comprises heating sucrose and an organic acid until fructose oligosaccharides are formed. This method produces a mixture of oligosaccharides, many of which differ in structure from the $GF_2$, $GF_3$, and $GF_4$ used in the present invention.

Richards et al. (WO 94/27618) disclosed a method for the treatment and prevention of diarrhea comprising administration of a caramel prepared according either to the process of U.S. Pat. No. 5,318,794 or according to the process of U.S. Pat. No. 5,206,355. WO 94/27618 provides examples of infants and adults suffering from diarrhea who were treated with the caramels. The present invention is, by contrast, directed to the prevention of otitis media in children by prophylactic administration of fructooligosaccharides.

Analysis of human breast milk has determined that it does not contain the FOS of this invention. Kunz and Rudloff have reported in an article entitled "Biological functions of oligosaccharides in human milk" Acta Paediatr. 82:903–12 (1993) that the monomers of breast milk oligosaccharides are D-glucose, D-galactose, N-acetylglucosamine, L-fucose and sialic acid. With few exceptions, all of the breast milk oligosaccharides carry lactose at their reducing end. In contrast, the present inventors have discovered that the very different fructooligosaccharides (FOS) with a degree of polymerization of from 2 to 20 can reduce the manifestation of otitis media in a human consuming from 0.5 to 5 grams per day FOS. In a more preferred embodiment, the human consumes 1.0 to 4.0 grams per day and in yet a still more preferred embodiment, the human consumes 1.5 to 3.5 grams per day of FOS.

Animal toxicology studies have shown no evidence of toxicity, mutagenicity, or carcinogenic effects due to FOS (Clevenger et al., "Toxicological evaluation of neosugar: genotoxicity, carcinogenicity, and chronic toxicity", *Journal of the American College of Toxicology* 7:643–662, 1988). FOS is used in Japan in many food products and has been added to infant formula. (Fructooligosaccharide Information Package, Coors BioTech, Inc. May 1990).

SUMMARY OF THE INVENTION

There is disclosed, a method of reducing the incidence of otitis media in a human, said method comprising enterally administering an effective amount of indigestible oligosaccharides to said human. This invention more specifically relates to a method of preventing otitis media in a human, said method comprises enterally administering from 0.5 grams to 5 grams per day of an indigestible oligosaccharide. The indigestible oligosaccharides useful in this invention are selected from fructooligosaccharides, fructosans, xylooligosaccharides and galactooligosaccharides. In a preferred embodiment, the fructooligosaccharides are selected from 1-kestose, nystose and 1-$^F$-β-fructofuranosyl nystose. The indigestible oligosaccharides are administered enterally in any convenient form. In one embodiment of the invention, the indigestible oligosaccharides are contained in a nutritional product such as infant formula. Enteral administration of the indigestible oligosaccharides can also be accomplished through their inclusion in products such as infant formula, 'follow-on' formula, toddler's beverages, milk, dietary supplements, fruit juice, fruit based drinks, candies, tablets, chewing gums, lozenges, yogurts, fermented products and the like. The term "fermented products" means products such as cottage cheese or fermented milk that use specified cultures of microorganisms in their manufacture. It has been found that administration of from 0.5 to 5 grams per day of the indigestible oligosaccharides will be efficacious in reducing the incidence of otitis media in a human.

In order to demonstrate the present invention a clinical study was undertaken to test whether the enteral administration of FOS would reduce the incidence of otitis media. A controlled 16 week, randomized blinded study was undertaken to determine if feeding indigestible oligosaccharides or fructooligosaccharides would reduce the incidence of otitis media in young children attending day care centers. Children were enrolled in the study and fed one of two study beverages: a milk-based beverage that served as a control or the same milk-based beverage containing FOS (Experimental). The study beverages were the sole source of milk fed to the children during the period of the study. The subjects were placed on active surveillance for illnesses including otitis media upon enrollment into the study. Results of the study show that the incidence of otitis media in subjects consuming FOS was significantly lower than in subjects consuming the control beverage.

DETAILED DESCRIPTION OF THE INVENTION

As used herein and in the claims "indigestible oligosaccharides" refers to carbohydrates with a degree of polymerization of from 2 to 20 ($GF_2$–$GF_{20}$) and l/or a molecular weight less than about 3,600 that is resistant to endogenous digestion in the human upper digestive tract. These "indigestible oligosaccharides" are utilized as a substrate for fermentation by selected bacteria like *lactobacilli and bifidobacteria* species and other nonpathogenic bacteria that reside in the lower gastrointestinal tract. Indigestible oligosaccharides that may be employed in the preferred embodiments of the invention may be prepared enzymatically, by chemical means or extracted from natural substances. As used herein and in the claims, effective amount of the indigestible oligosaccharide can range from 0.5–5 grams per day.

Chemical structures of sucrose and some fructooligosaccharides useful in the practice of the present invention are shown below. The structure of the general form is shown as $GF_n$, and the fructosan molecule is designated $F_m$. Any molecule depicted as $GF_n$, or $F_m$ can be used in the practice of the present invention. These include in the preferred embodiment 1-kestose ($GF_2$ in which one molecule of fructose is bound to sucrose), nystose ($GF_3$ in which two molecules of fructose are bound to sucrose), and 1-$^F$-β-fructofuranosyl nystose ($GF_4$ in which three molecules of fructose are bound to sucrose). In other embodiments of the invention indigestible oligosaccharides such as xylooligosaccharides and galactooligosaccharides will have a degree of polymerization ranging from 2 to 20. Xylooligosaccharides selected from the group consisting of xylobiose, xylotriose and xylotetrose are useful in the present invention. Xylooligosaccharides and galactooligosaccharides [(Galactose)$_n$-Galactose-Glucose] wherein N can range from 1 to 10 are also useful in the present invention.

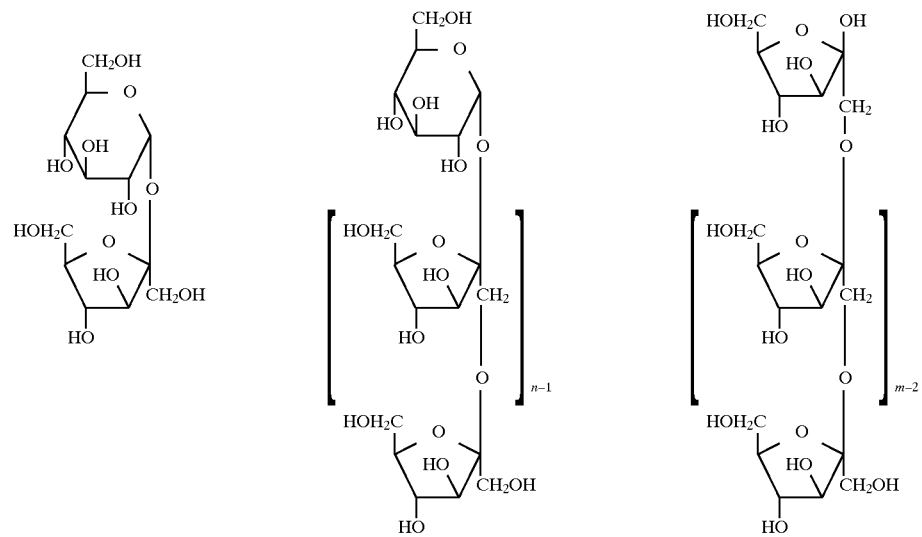

| Sucrose | $GF_n$ | $F_m$ |
|---|---|---|
| 1-ketose | nystose | $1^F$-β-fructo-furanosyl nystose |

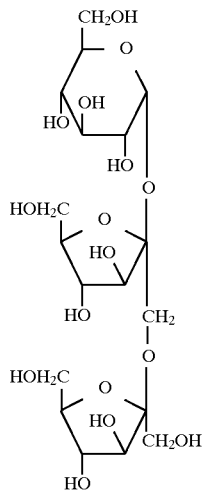
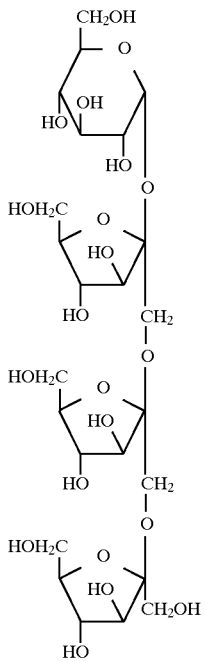
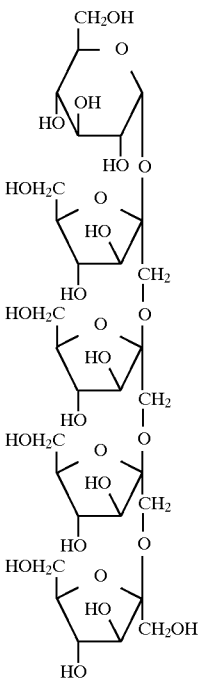

In general, the invention relates to a method of reducing the incidence of otitis media in a human, said method comprising enterally administering a therapeutically effective amount of an indigestible oligosaccharide to said human. The indigestible oligosaccharide is selected from the group consisting of fructooligosaccharides, fructosans, xylooligosaccharides and galactooligosaccharides having a degree of polymerization of 2 to 20.

METHODS AND MATERIALS

The indigestible oligosaccharides used in the clinical study were synthesized according to the method disclosed in U.S. Pat. No. 4,681,771 to Adachi et al. The teachings of U.S. Pat. No. 4,681,771 are incorporated herein by reference. The process comprises reacting sucrose in the presence of a fructosyltransferase from *Aspergillus niger* to obtain $GF_2$, $GF_3$, and $GF_4$. The FOS used in the clinical study was obtained from Golden Technologies, Inc. of Westminster, Colo. The Fructooligosaccharides Powder was Lot No. 931115 and had the following chemical analysis:

| | |
|---|---|
| Moisture | 2.5 |
| Carbohydrate composition (% dry basis) | |
| Glucose and Fructose | 0.5 |
| Sucrose | 3.5 |
| FOS | 96.0 |
| GF2 | 41.3 |
| GF3 | 45.7 |
| GF4 | 9.0 |

The Fructooligosaccharides Powder was a white powder with a granular size of less than 42 mesh. This FOS was used to prepare the milk-based fortified infant formula substantially in accordance with U.S. Pat. No. 5,021,245, the teachings of which are herein incorporated by reference. More specifically, to produce a 5,700 lb. batch of the powdered Experimental formula, a mixture of 20 lbs. of lactose, 1,100 lbs. of sucrose and 166 lbs. of FOS were dissolved in water. This carbohydrate solution was then combined with the protein, oils and vitamins set forth in Table 1, heat processed, homogenized, spray dried and packaged into containers.

Study Design

A controlled, blinded, randomized 16 week study was conducted on children attending day care centers. Children between 10 and 24 months of age were enrolled in the study and fed one of two beverages: a milk-based beverage that served as the control and was designated as Control; the same milk-based beverage that served as the Control formula was supplemented with FOS at 3.5 grams per liter and was designated as Experimental. Milk beverages other than the child's assigned study beverage were restricted. The study beverages were fed *ad libitum* as the sole source of milk.

At entry into the study, children were placed under active surveillance for otitis media and other significant medical illnesses. Surveillance included study evaluations at days 7, 28, 56, 84 and 112. Research nurses visited the participating day care centers each week to ensure study compliance and identify illness episodes.

Study Diet

The study beverages were powder products that were reconstituted with water at the point of consumption. The powdered Control and Experimental beverages were reconstituted by mixing 135 grams of powdered nutritional with 1 liter of water. The beverages contained approximately 670 to 725 Kcal per L.

The powdered products were provided in clinically labeled 400 gram cans. The beverage was a modified, fortified milk-based drink with or without FOS that met the nutrient levels recommended by the Committee on Nutrition of the American Academy of Pediatrics as required by the Infant Formula Act of 1980. The study beverage compositions are shown in Table 1.

Both beverages provided 20 calories per fluid ounce when reconstituted with water. The average daily intake for children receiving Control beverage was 750 mL and for children receiving Experimental beverage was 766 mL which resulted in consumption of approximately 2.6 grams of FOS per day.

TABLE 1

PRODUCT COMPOSITION
Approximate Composition of Study Beverage
With or Without Fructooligosaccharides (per liter)

| NUTRIENT | Experimental Study Beverage with Fructooligosaccharides | Control Study Beverage |
|---|---|---|
| Protein, g | 15.3 | 15.3 |
| Fat, g | 37.2 | 37.2 |
| Carbohydrate, g | 74.7 | 74.7 |
| Linolenic Acid, mg | 6500 | 6500 |
| Vitamin A, IU | 2900 | 2900 |
| Vitamin D, IU | 440 | 440 |
| Vitamin K, mcg | 112 | 112 |
| Thiamine ($B_1$), mcg | 239 | 239 |
| Riboflavin ($B_2$), mcg | 1505 | 1505 |
| Vitamin $B_{12}$, mcg | 3.24 | 3.24 |
| Niacin, mcg | 9000 | 9000 |
| Folic Acid (Folacin), mcg | 155 | 155 |
| Pantothenic Acid, mcg | 4250 | 4250 |
| Biotin, mcg | 45.0 | 45.0 |
| Vitamin C (Ascorbic Acid), mg | 150 | 150 |
| Choline, mg | 156 | 156 |
| Inositol, mg | 38 | 38 |
| Calcium, mg | 975 | 975 |
| Phosphorus, mg | 650 | 650 |
| Magnesium, mg | 75 | 75 |
| Iron, mg | 13 | 13 |
| Zinc, mg | 8.5 | 8.5 |
| Manganese, mcg | 52 | 52 |
| Copper, mcg | 710 | 710 |
| Sodium, mg | 220 | 220 |
| Iodine, mcg | 46 | 46 |
| Potassium, mg | 840 | 840 |
| Chloride, mg | 620 | 620 |
| Taurine, mg | 57.5 | 57.5 |
| Energy (Kcal) | 684 | 684 |
| β-Carotene, mcg | 400 | 400 |
| % Kcal from protein | 8.95 | 8.95 |
| Nucleotides, mg | 72 | 72 |
| FOS | 3.5 | 0 |

Study Subjects and Entry Procedures

Children were randomly assigned to receive Experimental or Control. The children were in apparent good health with no history of aspiration pneumonia, chronic gastroenteritis or diarrhea within seven days prior to enrollment. Subjects were prohibited from receiving human milk feedings for the duration of the study and had a history of ingesting whole cow's milk or cow's milk-based formula.

Day care center records and clinic or physician visits were monitored for clinically significant illnesses, such as diarrhea, bronchitis, bronchiolitis, and otitis media. Research nurses and physicians reviewed day care center records and clinic or physician records to document illnesses.

Statistical Methods

The number of children with otitis media and the number of episodes of otitis media in each feeding group were analyzed by the Cox regression analysis, using the marginal approach to multivariate survival analysis. The analysis of the number of episodes of otitis media counts all episodes including repeated episodes.

Incidence of Otitis Media

The incidence of otitis media in subjects consuming the experimental beverage containing FOS was significantly lower than in subjects consuming the Control beverage. Fifty subjects had documented episodes of otitis media during the course of the study: 17 of the 131 subjects receiving the Experimental beverage and 32 of the 134 subjects receiving Control. This is statistically significant with a probability of p=0.023. Results are summarized in Table 2.

TABLE 2

OTITIS MEDIA EPISODES

| | EXPERIMENTAL BEVERAGE N = 131 | CONTROL BEVERAGE N = 134 |
|---|---|---|
| NUMBER OF CHILDREN HAVING OTITIS MEDIA* | 17 | 33 |
| REPEAT EPISODES OF HAVING OTITIS MEDIA | 9 | 13 |
| TOTAL NUMBER OF EPISODES OF OTITIS MEDIA** | 26 | 51 |

*p = 0.023 by Cox Regression Analysis
**p = 0.0486 by Multivariant Cox Regression Analysis It is concluded from the results of the clinical study that administration of an indigestible oligosaccharide such as FOS reduces the incidence of otitis media in children. The reduced incidence of otitis media seen in the group of children fed FOS was unexpected. The prior art does not suggest or disclose that enteral administration of FOS would be effective in preventing the incidence of otitis media.

According to the present invention, it has been discovered that sugars selected from the indigestible oligosaccharides, particularly fructooligosaccharides can prevent the occurrence of otitis media.

The present invention provides a method for reducing the incidence of otitis media. Indigestible oligosaccharides can be added to various nutritional products including but not limited to infant formula and products for older children and adults, such as 'follow-on' formulas and toddler's beverages and also milk and yogurt products. They can be formulated in candies, tablets, lozenges, chewing gums and also mixed into dietary supplements and other liquid and powdered foods.

Industrial Applicability

The occurrence of otitis media is a major healthcare problem. The medical community has few tools to prevent and treat this disease, therefore the present invention will fulfill a long felt need. It is surprising that the enteral administration of naturally occurring indigestible oligosaccharides or sugars would be effective in reducing otitis media in humans.

While various embodiments of the present invention have been described in detail, it will be apparent to those skilled in the art that modifications and adaptations will occur to those skilled in the art. However, it is to be expressly understood that such modifications and adaptations are within the scope of the present invention, as set forth in the following claims.

What is claimed is:

1. A method of reducing the incidence of otitis media in a human said method comprising enterally administering an effective amount of a fructooligosaccharide selected from the group consisting of 1-kestose, nystose and $1\text{-}^F\text{-B-}$fructofuranosyl nystose.

2. The method of claim 1 wherein the fructooligosaccharide is administered in a nutritional product.

3. The method of claim 2, wherein the nutritional product is selected from the group consisting of an infant formula, follow-on formula, toddler's beverage, milk, yogurts, fermented products and dietary supplements.

4. The method of claim 2, wherein the nutritional product is selected from the group consisting of fruit juice and fruit-based drinks.

5. The method of claim 1, wherein the fructooligosaccharide is administered in a candy, a tablet, a chewing gum, a lozenge or a liquid.

6. The method of claim 1, wherein the fructooligosaccharide is administered at a rate of at least 0.5 grams per day to 5 grams per day.

7. The method of claim 2 wherein the nutritional product is selected from the group consisting of yogurts and fermented products.

8. A method of preventing otitis media in a human, said method comprising enterally administering to said human from 0.5 to 5 grams per day of at least one fructooligosaccharide selected from the group consisting of consisting of 1-kestose, nystose and $1\text{-}^F\text{-B-fructofuranosyl}$ nystose having a degree of polymerization of from 2 to 20.

9. A method according to claim 8 wherein the fructooligosaccharide is administered in a nutritional product.

10. A method according to claim 9 wherein the nutritional product is selected from the group consisting of an infant formula, follow-on formula, toddler's beverage, milk, yogurts, fermented products and dietary supplements.

11. A method according to claim 9 wherein the nutritional product is selected from the group consisting of fruit juice and fruit based drinks.

12. A method according to claim 8 wherein the fructooligosaccharide is administered in a candy, a tablet, a chewing gum, a lozenge or a liquid.

13. A method for reducing the occurrence of otitis media in a human, said method comprises enterally administering to said human at least 1 gram per day of at least one fructooligosaccharide selected from the group consisting of [$GF_2$, $GF_3$ and $GF_4$] 1-kestose, nytose and $1\text{-}^F\text{-}\beta\text{-}$fructofuranosyl nystose.

* * * * *